(12) United States Patent
Pandev et al.

(10) Patent No.: US 10,365,225 B1
(45) Date of Patent: Jul. 30, 2019

(54) MULTI-LOCATION METROLOGY

(71) Applicant: KLA-Tencor Corporation, Milpitas, CA (US)

(72) Inventors: Stilian Ivanov Pandev, Santa Clara, CA (US); Wei Lu, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 228 days.

(21) Appl. No.: 15/061,787

(22) Filed: Mar. 4, 2016

Related U.S. Application Data (60) Provisional application No. 62/128,257, filed on Mar. 4, 2015.

(51) Int. Cl.
| | |
|---|---|
| *G01B 11/00* | (2006.01) |
| *G01N 21/84* | (2006.01) |
| *H01L 21/67* | (2006.01) |

(52) U.S. Cl.
CPC ............. *G01N 21/84* (2013.01); *G01B 11/00* (2013.01); *G01N 21/8422* (2013.01); *H01L 21/67253* (2013.01); *G01N 2021/8416* (2013.01); *G01N 2201/12* (2013.01)

(58) Field of Classification Search
None
See application file for complete search history.

(56) References Cited

U.S. PATENT DOCUMENTS

| | | | |
|---|---|---|---|
| 5,608,526 | A | 3/1997 | Piwonka-Corle et al. |
| 5,859,424 | A | 1/1999 | Norton et al. |
| 6,192,103 | B1 * | 2/2001 | Wormington ........ G01N 23/207 378/73 |
| 6,429,943 | B1 | 8/2002 | Opsal et al. |
| 6,633,831 | B2 | 10/2003 | Nikoonahad et al. |
| 6,650,422 | B2 * | 11/2003 | Singh ..................... G01B 11/24 356/601 |
| 6,734,967 | B1 | 5/2004 | Piwonka-Corle et al. |
| 6,816,570 | B2 | 10/2004 | Janik et al. |

(Continued)

OTHER PUBLICATIONS

KLA-Tencor Announces Two Additions to Litho/Etch Process Control Portfolio, News Releast Feb. 25, 2013.*

(Continued)

*Primary Examiner* — J. E. Schoenholtz
(74) *Attorney, Agent, or Firm* — Spano Law Group; Joseph S. Spano (57) ABSTRACT

Methods and systems for estimating values of parameters of interest of structures fabricated on a wafer with a signal response metrology (SRM) model trained based on reference measurement data collected from the same wafer are presented herein. In one aspect, the SRM model is an input-output model trained to establish a functional relationship between reference measurements of structures fabricated on the wafer to raw measurement data collected from the same wafer. The raw measurement data collected from the wafer is employed for training the SRM model and for performing measurements using the trained SRM model. In another aspect, the SRM model uses the entire set of raw measurement data collected from a number of measurement sites across the wafer for both training and subsequent measurement at each individual site. In a further aspect, the SRM model is trained and utilized to measure each parameter of interest individually.

19 Claims, 4 Drawing Sheets

(56) References Cited

U.S. PATENT DOCUMENTS

| | | | |
|---|---|---|---|
| 6,895,075 B2 | 5/2005 | Yokhin et al. | |
| 6,972,852 B2 | 12/2005 | Opsal et al. | |
| 7,460,237 B1* | 12/2008 | Cramer | G03F 7/70625 355/55 |
| 7,478,019 B2 | 1/2009 | Zangooie et al. | |
| 7,747,424 B2* | 6/2010 | Opsal | G01B 11/24 703/13 |
| 7,826,071 B2 | 11/2010 | Shchegrov et al. | |
| 7,929,667 B1 | 4/2011 | Zhuang et al. | |
| 7,933,026 B2 | 4/2011 | Opsal et al. | |
| 8,843,875 B2 | 9/2014 | Pandev | |
| 2003/0200063 A1* | 10/2003 | Niu | G01B 11/00 703/2 |
| 2004/0235205 A1* | 11/2004 | Levy | G01N 21/211 438/14 |
| 2011/0246400 A1* | 10/2011 | Li | G01B 11/24 706/12 |
| 2012/0120396 A1* | 5/2012 | Kandel | G01B 11/24 356/399 |
| 2013/0114085 A1 | 5/2013 | Wang et al. | |
| 2013/0310966 A1* | 11/2013 | MacNaughton | G03F 7/70525 700/121 |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |
| 2016/0161248 A1* | 6/2016 | Zhang | G01B 11/14 356/601 |

OTHER PUBLICATIONS

Tzai, Wei-Jhe, et al. "Metrology of Advanced N14 Process Pattern Split at Lithography." Metrology, Inspection, and Process Control for Microlithography XXVIII, Feb. 2014, doi:10.1117/12.2046617.*

SpectraShape Family, Oct. 5, 2013, downloaded from URL<https://web.archive.org/web/20131005085433/https://www.kla-tencor.com/Metrology/spectrashape-family.html> on Jan. 22, 2018.*

Bashiri, M., and A. Farshbaf Geranmayeh. "Tuning the Parameters of an Artificial Neural Network Using Central Composite Design and Genetic Algorithm." Scientia Iranica, vol. 18, No. 6, 2011, pp. 1600-1608., doi:10.1016/j.scient.2011.08.031.*

Tzai, Wei-Jhe, et al. "Apply Multiple Target for Advanced Gate ADI Critical Dimension Measurement by Scatterometry Technology." Metrology, Inspection, and Process Control for Microlithography XXVI, 2012, doi:10.1117/12.916234.*

Product Overview of the SpectraCD 100 inline automated CD metrology, KLA-Tencor Mar. 2004.*

Apple II, with generic cassette drive, downloaded from URL<http://oldcomputers.net/appleii.html> on Aug. 6, 2018.*

Ge, Zhiqiang, and Zhihuan Song. "Semiconductor Manufacturing Process Monitoring Based on Adaptive Substatistical PCA." IEEE Transactions on Semiconductor Manufacturing, vol. 23, No. 1, 2010, pp. 99-108., doi:10.1109/tsm.2009.2039188.*

KLA-Tencor™ and TEL Announce New SpectraShape™ Dimensional Metrology Sysems With AcuShape Next-Generation Modeling Capability, Mar. 28, 2011 downloaded from URL<http://ir.kla-tencor.com/news-releases/news-release-details/kla-tencortm-and-tel-announce-new-spectrashapetm-dimensional> on Aug. 9, 2018.*

Pandev, Stilian, et al. "Signal Response Metrology (SRM): a New Approach for Lithography Metrology." Metrology, Inspection, and Process Control for Microlithography XXIX, 2015, doi:10.1117/12.2086056.*

Tzai, Wei-Jhe, et al. "Metrology of Advanced N14 Process Pattern Split at Lithography." Metrology, Inspection, and Process Control for Microlithography XXVIII, 2014, doi:10.1117/12.2046617.*

Yang, He Rong, et al. "Lithography Process Controllers and Photoresist Monitoring by Signal Response Metrology (SRM)." Metrology, Inspection, and Process Control for Microlithography XXIX, 2015, doi:10.1117/12.2085271.*

* cited by examiner

MULTI-LOCATION METROLOGY

CROSS REFERENCE TO RELATED APPLICATION

The present application for patent claims priority under 35 U.S.C. § 119 from U.S. provisional patent application Ser. No. 62/128,257, entitled "Multi-Location Metrology," filed Mar. 4, 2015, the subject matter of which is incorporated herein by reference in its entirety.

TECHNICAL FIELD

The described embodiments relate to metrology systems and methods, and more particularly to methods and systems for improved measurement of structures fabricated in the semiconductor industry.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

In some examples, optical critical dimension (CD) and film metrologies (spectroscopic or angle-resolved) are employed to monitor structural parameter values during manufacture to ensure that structures are fabricated having the desired pitch and profile. Often, however, the measurements of structures at different locations are performed separately. In other words, information gleaned from the measurement of a structure at one location is not utilized in the measurement of a repeated instance of the structure at another location. In addition, model-based metrology techniques include modeling errors induced by practical, computational limitations. For example, a number of parameters are fixed in a model-based measurement, so that regression calculations remain tractable. Hence, not all parameters are floated during computation, and this leads to errors in the estimates of parameter values.

Future metrology applications present challenges for metrology due to increasingly small resolution requirements, multi-parameter correlation, increasingly complex geometric structures, and increasing use of opaque materials. Thus, methods and systems for improved measurements are desired.

SUMMARY

Methods and systems for estimating values of parameters of interest of structures fabricated on a wafer with a signal response metrology (SRM) model trained based on reference measurement data collected from the same wafer are presented herein. The SRM model includes fewer errors than the reference measurements employed to train the SRM model.

In one aspect, the SRM model is an input-output model trained to establish a functional relationship between reference measurements of structures fabricated on the wafer to raw measurement data collected from the same wafer. The same raw measurement data collected from the same wafer is employed for training the SRM model and for performing measurements using the trained SRM model. By augmenting model-based metrology with a trained SRM model, overall measurement accuracy and precision are improved.

In another aspect, the SRM model uses the entire set of raw measurement data collected from a number of measurement sites across the wafer, or a subset of the wafer, for both training and subsequent measurement at each individual measurement site. As a result the SRM model captures parameter variations across the wafer, including random process and measurement errors. For example, processes change randomly (e.g., random focus and dosage errors, etc.) and the SRM models described herein are able to capture these errors.

In a further aspect, a SRM model is trained and utilized to measure each parameter of interest individually. Thus, the SRM model associated with each parameter of interest is optimized independently. By way of non-limiting example, the structures measured with a trained SRM model include line-space grating structures, FinFet structures, SRAM device structures, Flash memory structures, and DRAM memory structures.

The trained measurement models described herein receive optical measurement data directly as input and provide values of parameters of interest as output. By streamlining the measurement process, the predictive results are improved along with a reduction in computation and user time.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for estimating values of parameters of interest of structures fabricated on a wafer with a signal response metrology (SRM) model trained based on reference measurement data collected from the same wafer are presented herein. The SRM model includes fewer errors than the reference measurements employed to train the SRM model.

Parameter values estimated by model-based metrology systems include errors from a number of sources. For example, the underlying measurement model may not properly model certain aspects of the structure or the system (e.g., random process variations). In addition, the values of many measurement model parameters are fixed during regression calculations. Hence, not all measurement model parameters are floated during regression. This introduces errors in the estimation of parameters of interest. Furthermore, model truncation introduced in regression calculations introduces errors in the estimation of parameters of interest. These problems are magnified when measurements are performed on relatively small targets, such as static random access memory (SRAM) device targets. Other metrology systems, such as critical dimension scanning electron microscopy (CD-SEM) systems, provide high accuracy, but noisy measurements that result in precision errors.

In one aspect, the SRM model is an input-output model trained to establish a functional relationship between reference measurements of structures fabricated on the wafer to raw measurement data collected from the same wafer. The same raw measurement data collected from the same wafer is employed for training the SRM model and for performing measurements using the trained SRM model. By augmenting model-based metrology with a trained SRM model, overall measurement accuracy and precision are improved.

By using raw measurement data to train the SRM model, the errors and approximations associated with traditional model based metrology methods are reduced. In addition, the SRM model is not sensitive to systematic errors, asymmetries, etc. because the SRM model is trained based on raw measurement data collected from a particular metrology system and used to perform measurements based on the same measurement data. It should be noted that systematic errors that are embedded in the raw measurement data utilized for training the SRM model will not be captured by the trained SRM model. Thus, it is important to select a reference metrology system with systematic errors that are within acceptable limits for the particular measurement application under consideration.

Typically, measurements of parameters of interest performed at a particular measurement site rely on data collected from that particular measurement site only, even though data may be collected from multiple sites on the wafer. For example, a CD-SEM measurement relies on data collected from a specific measurement site. In other examples, model-based measurements, such as image-based overlay, scatterometry overlay, etc., use only a subset of the available measurement data for model based regression. Thus, information from multiple sites that may improve measurement performance is not used.

In another aspect, the SRM model uses the entire set of raw measurement data collected from a number of measurement sites across the wafer, or a subset of the wafer, for both training and subsequent measurement at each individual measurement site. As a result the SRM model captures parameter variations across the wafer, including random process and measurement errors. For example, processes change randomly (e.g., random focus and dosage errors, etc.) and the SRM models described herein are able to capture these errors.

In a further aspect, a SRM model is trained and utilized to measure each parameter of interest individually. Thus, the SRM model associated with each parameter of interest is optimized independently. By way of non-limiting example, the structures measured with a trained SRM model include line-space grating structures, FinFet structures, SRAM device structures, Flash memory structures, and DRAM memory structures.

Figure 1:
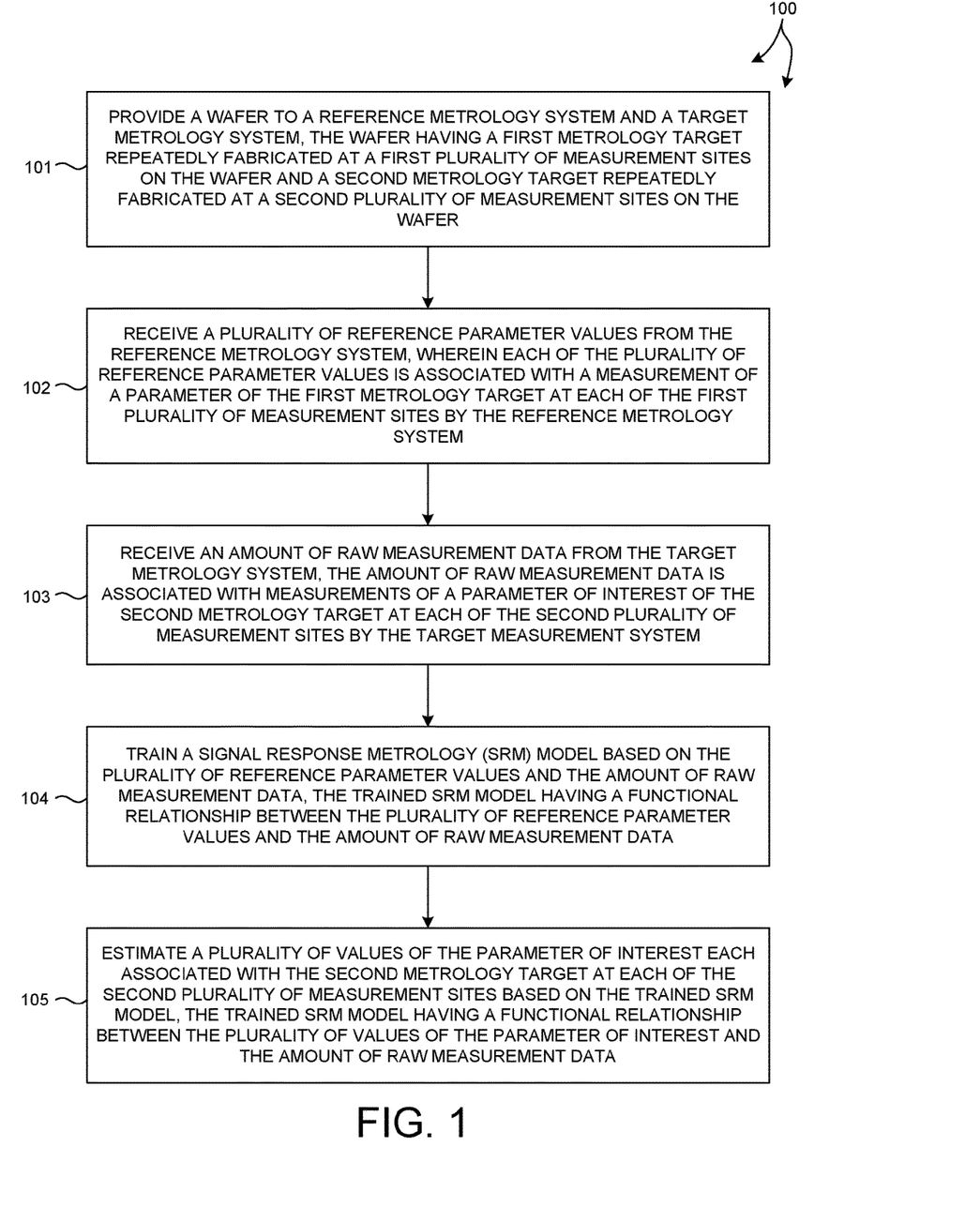
FIG. 1 illustrates a method 100 for estimating values of parameters of interest from measurements of structures fabricated on a wafer using a signal response metrology (SRM) model trained based on reference measurement data collected from the same wafer.

FIG. 1 illustrates a method 100 for estimating values of parameters of interest from measurements of structures fabricated on a wafer using a trained SRM model. Method 100 is suitable for implementation by a metrology system such as metrology system 300 illustrated in FIG. 3 of the present invention. In one aspect, it is recognized that data processing blocks of method 100 may be carried out via a pre-programmed algorithm executed by one or more processors of computing system 330, or any other general purpose computing system. It is recognized herein that the particular structural aspects of metrology system 300 do not represent limitations and should be interpreted as illustrative only. Training of the SRM model with data collected from a reference metrology tool is performed on each wafer to be measured by the SRM model, individually.

In block 101, a wafer is provided to a reference metrology system and a target metrology system. The wafer includes a first metrology target repeatedly fabricated at a first plurality of measurement sites on the wafer and a second metrology target repeatedly fabricated at a second plurality of measurement sites on the wafer. In some embodiments, the reference metrology system is the same system as the target metrology system. However, in some embodiments, the reference metrology system is different from the target metrology system. In some embodiments, the first metrology target and the second metrology target are the same target. However, in some other embodiments, they are different targets.

In block 102, a plurality of reference parameter values are received from the reference metrology system by a computing system (e.g., computing system 330). Each of the plurality of reference parameter values is associated with a measurement of a parameter of the first metrology target at each of the first plurality of measurement sites by the reference metrology system. By way of non-limiting example, reference parameters values may include critical dimension (CD), overlay, height, sidewall angle, edge placement error (EPE), pitch walk, etc.

In some embodiments, the measurement sites probed by the reference metrology system include structures having one or more parameters of interest that are measured by the reference metrology system. In general, the reference measurements may be performed by one or more reference metrology systems. By way of non-limiting example, scanning electron microscopy (SEM), atomic force microscopy (AFM), x-ray based metrology, such as small-angle x-ray scatterometry (SAXS), electrical measurement systems, and optical, model-based metrology techniques may be used alone, or in combination to generate the reference parameter values. The measurement by a reference metrology system may be performed either on device structures or on device-like structures located, e.g. in the scribeline area, to make them more suitable for reference metrology measurement.

In block 103, an amount of raw measurement data is received from the target metrology system by a computing system (e.g., computing system 330). The raw measurement data is associated with measurements of a parameter of interest of the second metrology target at each of the second plurality of measurement sites by the target measurement system. In some embodiments, the measurements are performed by an optically based metrology system (e.g., an optical scatterometer, an optical reflectometer, etc.). In general, the metrology targets probed by the target measurement system exhibit sensitivity to one or more parameters of interest. The measurements by the target measurement system may be performed either on device structures or on device-like structures located, e.g. in the scribeline area. In general, the measurement sites probed by the target measurement system may be the same or different from the measurement sites probed by the reference measurement system.

Figure 2:
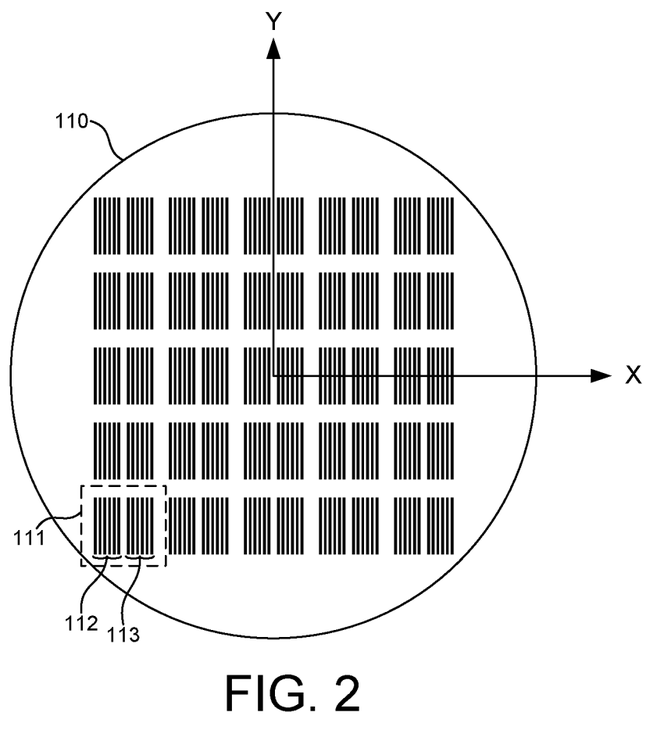
FIG. 2 depicts a wafer 120 having a grid of measurement sites 111 in one embodiment.

FIG. 2 depicts a wafer 120 having a grid of measurement sites 111. Each measurement site includes a reference target 112 measured by the reference measurement system and a measurement target 113 measured by the target measurement system. If a different target is employed for reference measurements than for target measurements, in general, it is preferable, to locate each reference target in close proximity to a corresponding measurement target. In this manner, process changes affect both the reference target and corresponding measurement target in a similar manner.

In general, raw measurement data collection and reference measurements may be performed across the entire wafer or a subset of the wafer area. In addition, the reference targets are designed for printability and sensitivity to changes in process parameters, structural parameters of interest, or both. In some examples, the reference targets are specialized targets that are not the same type as the corresponding measurement targets. In some embodiments, the reference targets are based on conventional line/space targets. By way of non-limiting example, CD targets, SCOL targets, or AiM™ targets available from KLA-Tencor Corporation, Milpitas, Calif. (USA) may be employed. In some other embodiments, the reference targets are device-like structures. In some other examples, the reference targets are device structures, or portions of device structures. Regardless of the type of reference target employed, a set of reference targets that exhibit sensitivity to the process variations, structural variations, or both, being explored must be provided to train the SRM model. Once the model is trained, it may be used to perform measurements of the same structure, or different structures having similar sensitivity.

In block 104, a SRM model is trained by a computing system (e.g., computing system 330) based on the plurality of reference parameter values and the amount of raw measurement data. The trained SRM model defines a functional relationship between the plurality of reference parameter values and the amount of raw measurement data collected by the target measurement system. In some examples, the SRM model is implemented as a neural network model. In other examples, the measurement model may be implemented as a linear model, a non-linear model, a polynomial model, a response surface model, a support vector machines model, or other types of models. In some examples, the measurement model may be implemented as a combination of models.

The model is trained such that its output fits the reference measurement values for the measured signals in the set of raw measurement data. In this manner, the trained measurement model maps the metrology signals measured with the target measurement system to the reference parameter values measured by the reference measurement system.

In block 105, a plurality of values of the parameter of interest is estimated by a computing system (e.g., computing system 330). Each value associated with the second metrology target at each of the second plurality of measurement sites is estimated based on the trained SRM model. The trained SRM model defines a functional relationship between the values of the parameter of interest and the amount of raw measurement data collected by the target measurement system.

Figure 3:
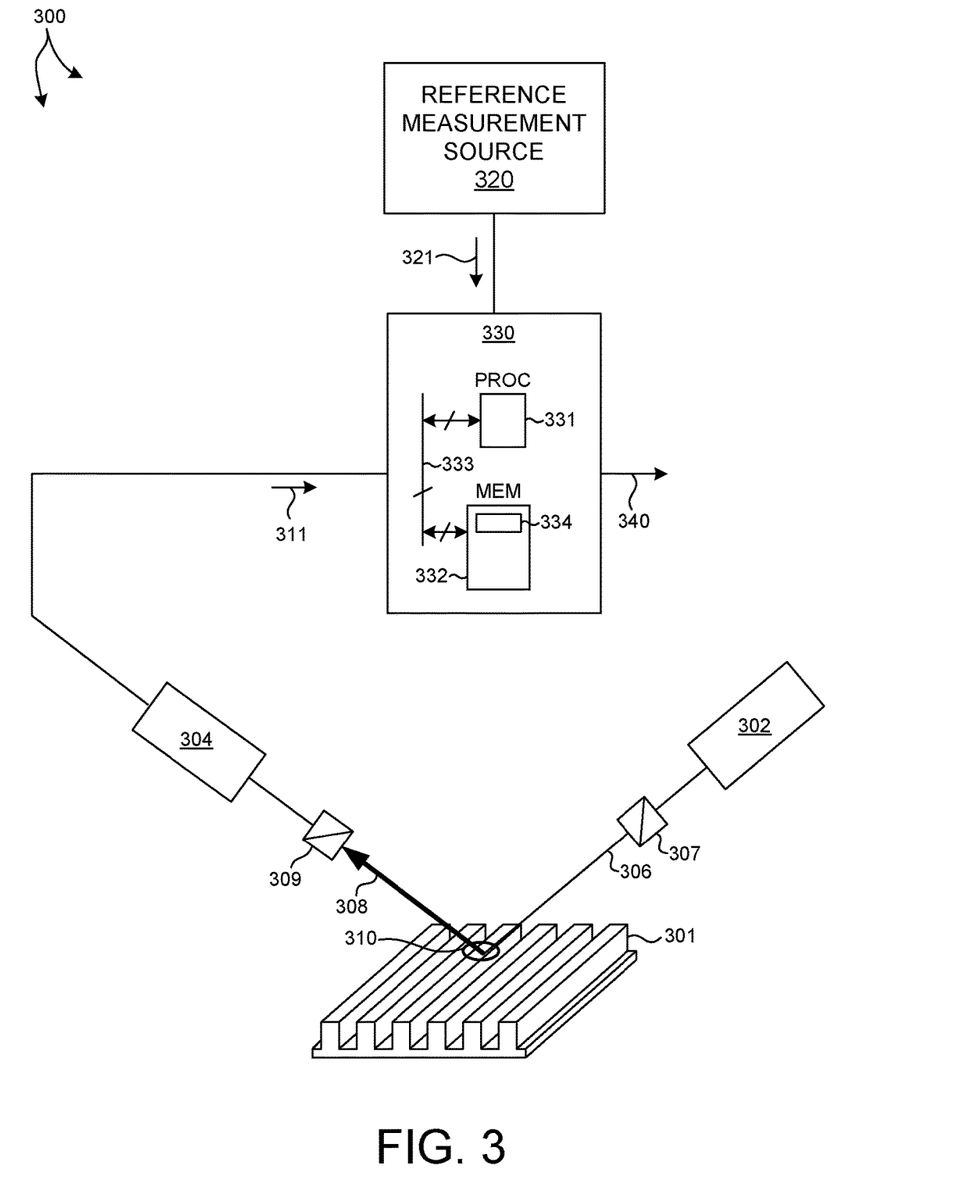
FIG. 3 depicts a metrology system 300 for measuring characteristics of a specimen in accordance with the exemplary methods presented herein.

In addition, the determined values of the parameter of interest are stored in a memory. For example, the values may be stored on-board the measurement system 300, for example, in memory 332, or may be communicated (e.g., via output signal 340) to an external memory device.

In some embodiments, the reference parameter is also the parameter of interest. Moreover, the reference parameter values are determined from the raw measurement data that is also employed to train the SRM model. In one embodiment, an optical scatterometry based, critical dimension (OCD) measurement system is employed to collect raw measurement data (e.g., spectral measurement data) from a number of targets located at different measurement sites across a wafer. The model-based OCD measurement system determines the value of a reference parameter (e.g., lithography focus) at each measurement site based on a regression analysis of the raw measurement data. As described hereinbefore, in general, the model-based OCD measurement system determines the reference parameter value for a particular measurement site based on the raw measurement data collected at that particular site, only. The SRM model is trained to establish a functional relationship between the raw measurement data and the reference parameter values determined at all of the measurement sites. The trained SRM model is then used to determine a more accurate estimate of the parameter of interest (e.g., lithography focus) at each measurement site with reduced overall error.

Figure 4:
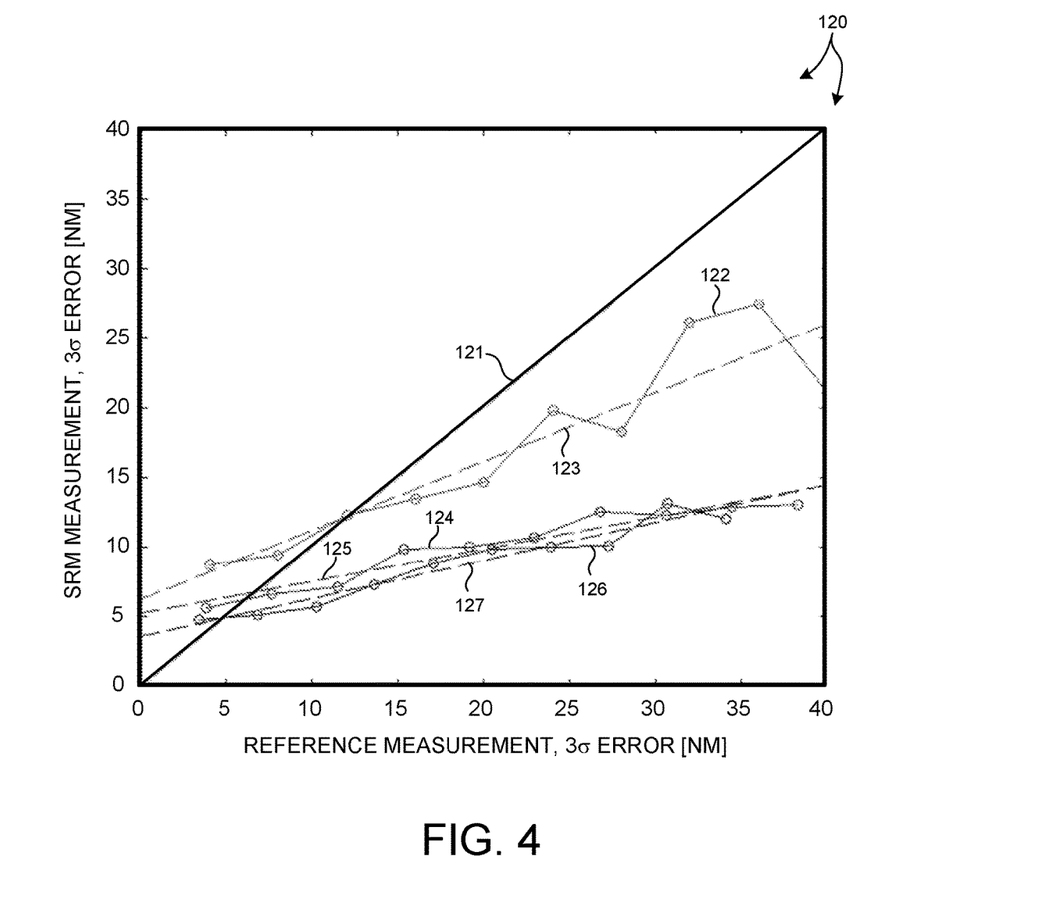
FIG. 4 illustrates a plot 120 comparing a simulation of lithography focus measurement errors generated by conventional model-based metrology and by a trained SRM model.

FIG. 4 illustrates a plot 120 comparing a simulation of lithography focus measurement errors generated by conventional model-based metrology and by a trained SRM model. As illustrated in FIG. 4, in general, the measurement errors associated with the SRM model are smaller than the model-based measurements employed as reference parameter values for training of the SRM model. The x-axis of plot 120 represents the three-sigma error associated with the measurement of lithography focus by the model-based, OCD measurement system described hereinbefore. The y-axis of plot 120 represents the three-sigma error associated with the estimates of lithography focus provided by the trained SRM model. The SRM model is trained based on the reference parameter values determined by the OCD measurement system and the raw measurement data collected by the OCD measurement system in the manner described herein. If the SRM model delivered exactly the same results as the model-based OCD measurement, the data points would all lie along line 121. However, this is not the case. Plotline 122 depicts the comparison of the SRM results with the model-based OCD results for measurements performed at one hundred different measurement sites. Plotline 123 depicts a linear fit of plotline 122. Plotline 124 depicts the comparison of the SRM results with the model-based OCD results for measurements performed at four hundred different measurement sites. Plotline 125 depicts a linear fit of plotline 124. Plotline 126 depicts the comparison of the SRM results with the model-based OCD results for measurements performed at nine hundred different measurement sites. Plotline 127 depicts a linear fit of plotline 126. As illustrated in FIG. 4, the reduction in measurement errors realized using the trained SRM model increases with more measurement samples. Thus, in general, collecting data from more measurement sites improves measurement results provided by the trained SRM model.

In another example, an image-based overlay measurement technique is employed as the reference measurement system and an optical scatterometry overlay system is employed as the target measurement system. Overlay error is typically evaluated based on measurements of specialized target structures formed at various locations on the wafer by a lithography tool. The target structures may take many forms, such as a box in box structure. In this form, a box is created on one layer of the wafer and a second, smaller box is created on another layer. The localized overlay error is measured by comparing the alignment between the centers of the two boxes. Such measurements are taken at locations on the wafer where target structures are available.

Image-based overlay metrology often requires the pattern to be resolved with an optical microscope that requires thick lines. The image-based measurements may be accurate, but noisy. Angle-resolved scatterometry overlay (SCOL) often produces much more repeatable measurement results.

In another example, a CD-SEM system is employed as the reference measurement system and an optical, model-based metrology system is employed as the target measurement system. In some examples, these metrologies are employed to measure overlay and EPE.

In some examples, the metrology target measured by the target measurement system is spatially separated from the reference target. The metrology target is selected to produce optical measurement signals with high sensitivity to parameters of interest such as overlay or EPE. However, the training or mapping is performed to actual device structures measured with reference tools such as CD-SEM, CD/OVL-SAXS, AFM, or model-based optical CD. After the mapping is performed, the parameters of interest are estimated based on the trained SRM model and the raw measurement data collected by the target measurement system.

In some other examples, the metrology target is separated from the reference target by time (i.e., separated by one or more process steps). In these examples, the training sequence can use the same or different types of targets that are separated by one or more processing steps from the actual device structure to be measured. In some examples, the metrology targets are actual device structures in a particular process state. Optical measurement data collected from actual device structures in a particular process state are used to train a SRM model as described herein. The trained measurement model is then used to calculate values of structural parameters, process parameters, or both, of the actual device structures in a subsequent process state.

In a further aspect, a separate SRM model is trained for each parameter of interest. In this manner, each SRM model is optimized individually for better performance with respect to each particular parameter of interest.

In general, the aforementioned measurement techniques may be applied to the measurement of process parameters, structural parameters, layout parameters, dispersion parameters, or any combination thereof. By way of non-limiting example, overlay, profile geometry parameters (e.g., critical dimension, height, sidewall angle), process parameters (e.g., focus, and dose), dispersion parameters, layout parameters (e.g., pitch walk, edge placement errors), or any combination of parameters may be measured using the aforementioned techniques. A set of reference targets and metrology targets with variations of each parameter of interest must be provided. Each measurement model is trained based on raw measurement data collected over the metrology targets and reference measurements of parameter values corresponding to each parameter of interest. With a measurement model trained for each parameter of interest, a single metrology target measurement can provide input to the measurement models to determined values of each parameter of interest.

In some examples, a SRM model is employed to measure a process parameter of interest (e.g., focus/dose, exposure, etc.), and another SRM model is employed to measure a structural parameter of interest (e.g., EPE, overlay, CD, pitch walk, etc.).

In some embodiments, the same raw measurement data is used to create different SRM models for measuring different parameters of interest. Each SRM model is trained using a different set of reference parameter values corresponding to each different parameter of interest.

In another further aspect, the metrology targets located on the wafer are preferably design rule targets. In other words, the metrology targets adhere to the design rules applicable to the underlying semiconductor manufacturing process. In some examples, the metrology targets are preferably located within the active die area. In some examples, the metrology targets have dimensions of 15 µm by 15 µm, or smaller. In this manner, the impact on overlay of intra-field variations induced by lithographic imperfections can be analyzed. In some other examples, the metrology targets are located in the scribe lines, or otherwise outside the active die area.

The trained SRM models described herein receive raw measurement data directly as input and provide values of parameters of interest as output. By streamlining the measurement process, the predictive results are improved along with a reduction in computation and user time. In some examples, the SRM model can be created in less than an hour. In addition, by employing a simplified model, measurement time is reduced compared to existing metrology methods.

In another further aspect, the methods and systems for training the SRM model include an optimization algorithm to automate any or all of the elements required to arrive at a trained measurement model.

In some examples, an optimization algorithm is configured to maximize the performance of the measurement (defined by a cost function) by optimizing any or all of the following parameters: the type of measurement model and the parameters of the selected measurement model. The optimization algorithm can include user defined heuristics and can be combination of nested optimizations (e.g., combinatorial and continuous optimization).

In a further aspect, optical measurement data from multiple, different targets is collected for model building, training, and measurement. The use of data associated with multiple targets having different structure, but formed by the same process conditions increases the information embedded in the model and reduces the correlation to process or other parameter variations. The additional information embedded in the model allows for a decoupling of information content associated with one parameter of interest from information associated with other parameters (e.g., film thicknesses, CD, etc.) that may affect the measured signals in a similar manner. In these examples, the use of training data that includes measurements of multiple, different targets at one or more measurement sites enables more accurate parameter estimation. In some examples, a mixture of isolated and dense line/space targets is employed to decouple overlay from underlayer effects. In some examples, multiple, different targets offset in orthogonal directions are employed in each die. This may be advantageous to minimize the effects of underlayers on measurement accuracy. In one example, SRAM device area can be used as one metrology target because it is sensitive to CD changes in combination with another metrology target sensitive to overlay.

In general, any measurement technique, or combination of two or more measurement techniques may be contemplated within the scope of this patent document as the data processed by the SRM model for training and measurement is in vector form. Because the signal response metrology techniques as described herein operate on vectors of data, each collected signal is treated independently. In addition, it is possible to concatenate data from multiple, different metrologies, regardless of whether the data is two dimensional data, one dimensional data, or even single point data.

Exemplary measurement techniques that may provide data for analysis in accordance with the signal response metrology techniques described herein include, but are not limited to spectroscopic ellipsometry, including Mueller matrix ellipsometry, spectroscopic reflectometry, including single wavelength, multiple wavelength, and angle resolved, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), raman spectroscopy, x-ray fluorescence (XRF), grazing incidence x-ray fluorescence (GIXRF), x-ray tomography, and x-ray ellipsometry. In general, any metrology technique applicable to the characterization of semiconductor structures, including image based metrology techniques, speckle based scatterometers, scanning electron microscopy (SEM), tunneling electron microscopy (TEM), and atomic force microscopy (AFM), may be contemplated, individually, or in any combination.

In general, signals from multiple targets each measured by multiple metrology techniques increases the information content in the combined set of signals and reduces the correlation to process or other parameter variations.

In a further aspect, the methods and systems for training and measuring actual device structures as described hereinbefore are implemented in a differential mode. In such a scheme the metrology target measurements and any associated reference measurements are performed at two distinct steps in the processing flow. The differences in the measured signals at each distinct processing step are treated as training signals for training purposes and measurement signals for measurement purposes.

In one example, the same location points are used for metrology target measurements at a lithography step and a subsequent etch step. The difference signal between the lithography and etch steps allows for monitoring of process variability on a per point site basis even if the structure varies between points on the wafer (e.g., due to process steps or small positioning errors). Such differential metrology mode may be preferred for metrology of SRAM device area where variations of the measurement target are present between different fields on the wafer.

In some examples, variations of the measurement target arise from a deficiency in the periodicity of the measured structures, e.g., finite structure size or in situations where the otherwise periodic structure is insufficiently repeated within the measurement spot of the metrology system. In some examples, variations of the measurement target arise from a small spot size of the optical metrology system and measurement location placement errors of the metrology system.

In some examples, the differences between actual device parameter values before and after one or more etch steps may be used as an input to the closed loop control of the etch process.

In general, differential SRM metrology allows for global (wafer), field (field average), or local (per site) results that can be used, for example, to set the target bias between two process monitoring steps (i.e., etch and lithography), provide per field correction, or provide high order correction (e.g., OVL or EPE control).

FIG. 3 illustrates a system 300 for measuring characteristics of a specimen in accordance with the exemplary methods presented herein. As shown in FIG. 3, the system 300 may be used to perform spectroscopic ellipsometry measurements of one or more structures of a specimen 301. In this aspect, the system 300 may include a spectroscopic ellipsometer equipped with an illuminator 302 and a spectrometer 304. The illuminator 302 of the system 300 is configured to generate and direct illumination of a selected wavelength range (e.g., 100-2500 nm) to the structure disposed on the surface of the specimen 301. In turn, the spectrometer 304 is configured to receive illumination reflected from the surface of the specimen 301. It is further noted that the light emerging from the illuminator 302 is polarized using a polarization state generator 307 to produce a polarized illumination beam 306. The radiation reflected by the structure disposed on the specimen 301 is passed through a polarization state analyzer 309 and to the spectrometer 304. The radiation received by the spectrometer 304 in the collection beam 308 is analyzed with regard to polarization state, allowing for spectral analysis by the spectrometer of radiation passed by the analyzer. These spectra 311 are passed to the computing system 330 for analysis of the structure.

As depicted in FIG. 3, system 300 includes a single measurement technology (i.e., SE). However, in general, system 300 may include any number of different measurement technologies. By way of non-limiting example, system 300 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 300 may include one or more computing systems 330 employed to perform measurements of actual device structures based on measurement models developed in accordance with the methods described herein. The one or more computing systems 330 may be communicatively coupled to the spectrometer 304. In one aspect, the one or more computing systems 330 are configured to receive measurement data 311 associated with measurements of the structure of specimen 301.

It should be recognized that the various steps described throughout the present disclosure may be carried out by a single computer system 330 or, alternatively, a multiple computer system 330. Moreover, different subsystems of the system 300, such as the spectroscopic ellipsometer 304, may include a computer system suitable for carrying out at least a portion of the steps described herein. Therefore, the aforementioned description should not be interpreted as a limitation on the present invention but merely an illustration. Further, the one or more computing systems 330 may be configured to perform any other step(s) of any of the method embodiments described herein.

In addition, the computer system 330 may be communicatively coupled to the spectrometer 304 in any manner known in the art. For example, the one or more computing systems 330 may be coupled to computing systems associated with the spectrometer 304. In another example, the spectrometer 304 may be controlled directly by a single computer system coupled to computer system 330.

The computer system 330 of the metrology system 300 may be configured to receive and/or acquire data or information from the subsystems of the system (e.g., spectrometer 304 and the like) by a transmission medium that may include wireline and/or wireless portions. In this manner, the transmission medium may serve as a data link between the computer system 330 and other subsystems of the system 300.

Computer system 330 of the integrated metrology system 300 may be configured to receive and/or acquire data or information (e.g., measurement results, modeling inputs, modeling results, reference measurement data 321, etc.) from other systems by a transmission medium that may include wireline and/or wireless portions. In this manner, the transmission medium may serve as a data link between the computer system 330 and other systems (e.g., memory on-board metrology system 300, external memory, reference measurement source 320, or other external systems). For example, the computing system 330 may be configured to receive measurement data from a storage medium (i.e., memory 332 or an external memory) via a data link. For instance, spectral results obtained using spectrometer 304 may be stored in a permanent or semi-permanent memory device (e.g., memory 332 or an external memory). In this regard, the spectral results may be imported from on-board memory or from an external memory system. In another example, the computing system 330 may be configured to receive reference measurement data 321 from a reference measurement source (e.g., a storage medium) via a data link. For instance, reference measurement results obtained using a reference measurement system may be stored in a permanent or semi-permanent memory device. In this regard, the reference measurement results may be imported from on-board memory or from an external memory system. Moreover, the computer system 330 may send data to other systems via a transmission medium. For instance, a SRM model or an actual device parameter value 340 determined by computer system 330 may be communicated and stored in an external memory. In this regard, measurement results may be exported to another system.

Computing system 330 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 334 implementing methods such as those described herein may be transmitted over a transmission medium such as a wire, cable, or wireless transmission link. For example, as illustrated in FIG. 3, program instructions 334 stored in memory 332 are transmitted to processor 331 over bus 333. Program instructions 334 are stored in a computer readable medium (e.g., memory 332). Exemplary computer-readable media include read-only memory, a random access memory, a magnetic or optical disk, or a magnetic tape.

In some examples, the model building, training, and measurement methods described herein are implemented as an element of a SpectraShape® optical critical-dimension metrology system available from KLA-Tencor Corporation, Milpitas, Calif., USA. In this manner, the model is created and ready for use immediately after the required reference data and raw measurement data are collected by the system.

In some other examples, the model building and training methods described herein are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

In yet another aspect, the SRM model results described herein can be used to provide active feedback to a process tool (e.g., lithography tool, etch tool, deposition tool, etc.). For example, values of EPE or overlay error determined using the methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

In general, the systems and methods described herein may be implemented as part of the process of preparing a SRM model for off-line or on-tool measurement.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A measurement system comprising:
   a reference metrology system configured to perform a plurality of measurements of a first metrology target at a first plurality of measurement sites on a wafer and generate a plurality of reference parameter values, wherein each of the plurality of reference parameter values corresponds to a measurement at each of the first plurality of measurement sites;
   a target metrology system configured to perform a plurality of measurements of a second metrology target at a second plurality of measurement sites on the wafer and generate an amount of raw measurement data corresponding to the plurality of measurements of the second metrology target; and
   a computing system configured to:
   receive the plurality of reference parameter values from the reference metrology system;
   receive the amount of raw measurement data from the target metrology system;
   train a signal response metrology (SRM) model based on the plurality of reference parameter values and the amount of raw measurement data, the trained SRM model having a functional relationship between the plurality of reference parameter values and the amount of raw measurement data and;
   estimate a plurality of values of a parameter of interest each associated with the second metrology target at each of the second plurality of measurement sites based on the trained SRM model.

2. The measurement system of claim 1, wherein the second metrology target is the first metrology target.

3. The measurement system of claim 1, wherein the second plurality of measurement sites is the first plurality of measurement sites.

4. The measurement system of claim 1, wherein the parameter of interest of the second metrology target is the reference parameter of the first metrology target measured by the reference metrology system.

5. The measurement system of claim 1, wherein the reference metrology system is the target metrology system.

6. The measurement system of claim 5, wherein the reference metrology system is a model-based metrology system.

7. The measurement system of claim 1, wherein the SRM model is any of a linear model, a nonlinear model, a polynomial model, a neural network model, a support vector machines model, a decision tree model, and a random forest model.

8. The measurement system of claim 1, wherein the parameter of interest is any of a structural parameter, a process parameter, a layout parameter, an overlay parameter, and a dispersion parameter.

9. The measurement system of claim 1, wherein the amount of raw measurement data includes a combination of measurements of a plurality of different metrology targets formed by the same process conditions.

10. The measurement system of claim 1, wherein the amount of raw measurement data includes measurements acquired by a plurality of different metrology techniques.

11. A method comprising:
providing a wafer to a reference metrology system and a target metrology system, the wafer having a first metrology target repeatedly fabricated at a first plurality of measurement sites on the wafer and a second metrology target repeatedly fabricated at a second plurality of measurement sites on the wafer;
receiving a plurality of reference parameter values from the reference metrology system, wherein each of the plurality of reference parameter values is associated with a measurement of a parameter of the first metrology target at each of the first plurality of measurement sites by the reference metrology system;
receiving an amount of raw measurement data from the target metrology system, the amount of raw measurement data is associated with measurements of a parameter of interest of the second metrology target at each of the second plurality of measurement sites by the target measurement system;
training a signal response metrology (SRM) model based on the plurality of reference parameter values and the amount of raw measurement data, the trained SRM model having a functional relationship between the plurality of reference parameter values and the amount of raw measurement data and;
estimating a plurality of values of the parameter of interest each associated with the second metrology target at each of the second plurality of measurement sites on the wafer based on the trained SRM model, wherein the parameter of interest is any of a structural parameter, a process parameter, a layout parameter, an overlay parameter, and a dispersion parameter.

12. The method of claim 11, wherein the first and second metrology targets are the same target, the first plurality of measurement sites and the second plurality of measurement sites are the same measurement sites, and the parameter of interest of the second metrology target is the same parameter as the parameter of the first metrology target.

13. The method of claim 11, wherein the reference metrology system and the target metrology system are the same model-based metrology system.

14. The method of claim 11, wherein the SRM model is any of a linear model, a nonlinear model, a polynomial model, a neural network model, a support vector machines model, a decision tree model, and a random forest model.

15. The method of claim 11, wherein the first metrology target, the second metrology target, or both, is an actual device structure.

16. The method of claim 11, wherein the amount of raw measurement data includes a combination of measurements of a plurality of different metrology targets formed by the same process conditions.

17. The method of claim 11, wherein the amount of raw measurement data includes measurements acquired by a plurality of different metrology techniques.

18. The measurement system of claim 1, the computing system further configured to:
communicate an indication of the values of the parameter of interest to a semiconductor fabrication tool that causes the semiconductor fabrication tool to adjust one or more parameters of a fabrication process of the semiconductor fabrication tool.

19. The method of claim 11, further comprising:
communicating an indication of the values of the parameter of interest to a semiconductor fabrication tool that causes the semiconductor fabrication tool to adjust one or more parameters of a fabrication process of the semiconductor fabrication tool.

* * * * *